United States Patent [19]

Sabahi et al.

[11] Patent Number: 5,569,779
[45] Date of Patent: Oct. 29, 1996

[54] POLYFUNCTIONAL MICHAEL ADDITION PRODUCTS

[75] Inventors: Mahmood Sabahi, Baton Rouge, La.; Matthew L. Hurst, Warren, Ohio

[73] Assignee: Albemarle Corporation, Richmond, Va.

[21] Appl. No.: 481,953

[22] Filed: Jun. 7, 1995

Related U.S. Application Data

[60] Continuation-in-part of Ser. No. 169,287, Dec. 20, 1993, abandoned, which is a division of Ser. No. 947,629, Sep. 21, 1992, abandoned, which is a continuation-in-part of Ser. No. 812,398, Dec. 23, 1991, abandoned.

[51] Int. Cl.$^6$ ................................................. C07C 69/34
[52] U.S. Cl. ................................................. 560/190
[58] Field of Search ................................. 560/190

[56] References Cited

U.S. PATENT DOCUMENTS

| | | | |
|---|---|---|---|
| 2,396,626 | 3/1946 | Wiest et al. | 260/464 |
| 4,795,787 | 1/1989 | Walz | 525/328.2 |

FOREIGN PATENT DOCUMENTS 238578  8/1990  Japan.

OTHER PUBLICATIONS

Skarzewski, "The Michael Reaction of Methanetricarboxylic Esters. A Simple method for Two–Carbon Chain Elongation", Synthesis, Dec. 1990, pp. 1125–1127.

Search Report, CA83(4):3032Aq (Lorenz et al., DE 2342539, Mar. 1975).

Derwent Database: –85–143009 (Denki Kagaku, JP 60–076504 (May 1975).

*Primary Examiner*—Samuel Barts
*Attorney, Agent, or Firm*—Philip M. Pippenger

[57] ABSTRACT

Compound mixtures varying from liquids to solids can be prepared via a Michael reaction so that (1) their molecules correspond to the formula $Z-C(E)E')_p-Q_s$ wherein Z is alkyl, cycloalkyl, or $-(CTT'-CT''G)_w-CTT'-CHT''G$; Q is $-(CTT'-CT''G)_t-CTT'-CHT''G$; T, T', and T'' are independently selected from hydrogen, G', and hydrocarbyl or predominantly hydrocarbyl organic groups containing up to 10 carbons, with the proviso that at least one of T, T', and T'' must be hydrogen; E, E', G, and G' are independently selected from $-COOR$, $-C(O)R'$, and $-CN$ electron withdrawing groups in which R and R' represent alkyl or cycloalkyl groups of up to 10 carbons; p is zero or one; s is respectively two or one; and each of t and w represents zero or a positive integer and (2) at least 25% of the molecules contain at least three G groups. Among the more preferred products are the ester oils in which the esterifying groups contain 1–10 carbons and which have viscosities such as to make them suitable for use as lubricants.

14 Claims, No Drawings

POLYFUNCTIONAL MICHAEL ADDITION PRODUCTS

Cross-Reference to Related Application

This application is a continuation-in-part of application Ser. No. 08/169,287, filed Dec. 20, 1993, now abandoned which in turn is a division of Ser. No. 07/947,629, filed Sep. 21, 1992, now abandoned which in turn is a continuation-in-part of Ser. No. 07/812,398, filed Dec. 23, 1991 now abandoned.

FIELD OF INVENTION

The invention relates to Michael addition products. More particularly, it relates to such products in which at least 25% of the molecules contain at least three moieties derived from the Michael acceptor.

BACKGROUND

The Michael reaction is a known process wherein a Michael acceptor (such as an $\alpha,\beta$-ethylenically-unsaturated aldehyde, ester, nitrile, ketone, sulfone, or sulfoxide) is reacted with a Michael donor (such as a dialkyl malonate) to elongate a carbon chain. U.S. Pat. No. 2,396,626 (Wiest et al.) teaches that useful products can be obtained by reacting two molecules of acrylonitrile, an alkyl acrylate, or an acrylamide with a molecule of a donor, such as an ester, amide, or nitrile of malonic acid, phenylacetic acid, cyanoacetic acid, or acetoacetic acid. However, as indicated in Skarzewski, "The Michael Reaction of Methanetricarboxylic Esters. A Simple Method for Two-Carbon Chain Elongation," *Synthesis*, December 1990, pp. 1125–1127, it has usually been considered undesirable to add a donor molecule to more than one acceptor molecule in such a reaction.

SUMMARY OF INVENTION

It has been found that useful products can be obtained by conducting the reactions between suitable Michael donors and acceptors so as to form mixtures of compounds in which at least 25% of the molecules contain at least three moieties derived from the Michael acceptors. Thus, the invention resides in mixtures of compounds corresponding to the formula Z—C(E)(E')$_p$—Q$_s$ wherein Z is alky 1, cycloalkyl, or —(CTT'—CT"G)$_w$—CTT'—CHT"G; Q is —(CTT'—CT"G)$_t$—CTT'—CHT"G; T, T', and T" are independently selected from hydrogen, G', and organic groups containing up to 10 carbons, with the proviso that at least one of T, T', and T" must be hydrogen; E, E', G, and G' are independently selected from —COOR, —C(O)R', and —CN electron withdrawing groups in which R and R' represent alkyl or cycloalkyl groups of up to 10 carbons; p is zero or one; s is respectively two or one; and each oft and w represents zero or a positive integer; at least 25% of the molecules of the compounds containing at least three G groups.

DETAILED DESCRIPTION

As already mentioned, the products of the invention are obtained by the reaction between suitable Michael donors and acceptors. These donors and acceptors are compounds which have one or more electron withdrawing groups attached to an organic group which is hydrocarbyl or at least predominantly hydrocarbyl in nature, i.e., (1) contains only carbon and hydrogen or (2) contains carbon, hydrogen, and one or more other atoms but contains so few of the other atoms that the predominantly hydrocarbyl nature of the group is preserved.

When a predominantly hydrocarbyl R or R' group (or any other predominantly hydrocarbyl group mentioned hereinafter) contains atoms other than carbon and hydrogen, these other atoms may be part of a chain or ring as hetero atoms, such as oxygen, sulfur, or phosphorus atoms; or they may be present in substituent groups, such as alkoxy, halo, or cyano groups. However, to preserve the predominantly hydrocarbyl nature of the group, the number of hetero atoms or non-hydrocarbyl substituents therein should not exceed 0.3 per carbon and is preferably not more than 0.1 per carbon. These predominantly hydrocarbyl groups can be regarded as being virtually the same as the alkyl, cycloalkyl, aralkyl, and alkenyl groups to which they most closely correspond, so terms such as alkyl, cycloalkyl, aralkyl, and alkenyl, as used hereinafter, should be understood as including the predominantly hydrocarbyl groups as well as the hydrocarbyl groups normally denoted by those terms (except, of course, when the terms are qualified in such a way as to make it clear that they could not refer to the predominantly hydrocarbyl groups—as when the groups contain too few carbons to permit the inclusion of any hetero atoms while fulfilling the requirement of containing $\leq 0.3$ such atoms per carbon.)

In each of the reactants employed to prepare the products of the invention, the electron withdrawing groups are selected from —COOR, —C(O)R', and —CN groups in which R and R' represent alkyl or cycloalkyl groups of up to 10 carbons. The electron withdrawing groups may be the same or different, whether they are present in the same reactant or in different reactants.

Michael donors which can be used in the reaction are compounds corresponding to the formula Z'—CH(E)(E") wherein Z' is hydrogen or an alkyl or cycloalkyl group of up to 10 carbons, E is a —COOR, —C(O)R', or —CN electron withdrawing group, and E" is hydrogen or a —COOR, —C(O)R', or —CN electron withdrawing group —R and R' in these formulas representing alkyl or cycloalkyl groups of up to 10 carbons, preferably methyl or ethyl. When a single Michael donor is employed in the reaction, each E in the Z—C(E)(E')$_p$—Q$_s$ product is the same, as is each E' in that product. However, when a mixture of two or more donors is used, different molecules of the product will contain different E and/or E' groups when the donors contain different E and/or E" groups.

Exemplary of utilizable donors are (1) the methyl, ethyl, propyl, isopropyl, butyl, isobutyl, t-butyl, pentyl, hexyl, chlorohexyl, heptyl, octyl, decyl, bromodecyl, ethoxyoctyl, cyclopropyl, cyclopentyl, cyclohexyl, and cyclooctyl esters of alkanoic and substituted alkanoic acids such as acetic, cyanoacetic, propionic, and butyric acids, (2) the corresponding diesters of 1,1-dicarboxyalkanes and other dicarboxyalkanes (e.g., succinic, glutaric, and higher acids of the oxalic acid series) in which the alkane moiety is a divalent hydrocarbylene radical derived from an alkane such as methane, ethane, propane, isopropane, butane, isobutane, t-butane, pentane, hexane, heptane, octane, propoxypentane, butoxypentane, nonane, decane, or ethoxyoctane; (3) the corresponding diesters of 1,1-dicarboxy-1-cycloallcyl-methanes in which the cycloallcyl substituent is cyclopropyl, cyclopentyl, cyclohexyl, or cyclooctyl; (4) the corresponding dicyano- and diacyl-substituted alkanes and cycloalkylmethanes in which the acyl groups are acetyl, propionyl, butyryl, or isobutyryl; and (5) the corresponding cyano- or acyl-substituted alkanoic and cycloalkylethanoic acid esters. The most preferred Michael donors are the dimethyl and diethyl malonates; the methyl and ethyl cyanoacetates, acetoacetates; propionylacetates; malononitrile; acetonitrile; and dipropionylmethane.

Michael acceptors which may be reacted with these donors are CTT"=CT"G compounds in which T, T', and T" are independently selected from hydrogen, G', and organic groups (usually hydrocarbyl or predominantly hydrocarbyl groups, such as alkyl, alkoxyalkyl, alkylthioalkyl, cycloalkyl, dialkylaminocycloalkyl, aryl, haloaryl, alkoxyaryl, aralkyl, and alkaryl groups) of up to 10 carbons, with the proviso that at least one of T, T', and T" must be hydrogen; and G and G' are electron withdrawing groups selected from the —COOR, —C(O)R', and —CN groups described above.

Examples of utilizable acceptors are (1) the methyl, ethyl, propyl, isopropyl, butyl, isobutyl, t-butyl, pentyl, hexyl, chlorohexyl, heptyl, octyl, decyl, bromodecyl, ethoxyoctyl, cyclopropyl, cyclopentyl, cyclohexyl, and cyclooctyl esters of acrylic, methacrylic, ethacrylic, crotonic, and cinnamic acids, (2) the corresponding esters of 1-carboxy-1-cyanoethylene and the corresponding diesters of 1,1-dicarboxy-2-cyanoethylene and 1,1-dicarboxyethylene, and (3) nitriles such as acrylonitrile, methacrylonitrile, ethacrylonitrile, dicyanoethylene, and tricyanoethylene, as well as the corresponding compounds in which the α- or β-carbon bears an organic substituent such as a propyl, isopropyl, butyl, isobutyl, t-butyl, pentyl, hexyl, chlorohexyl, heptyl, octyl, ethylthiohexyl, decyl, bromodecyl, cyanodecyl, ethoxyoctyl, cyclopropyl, cyclopentyl, cyclohexyl, cyclooctyl, N,N-dimethylaminocyclohexyl, methylphenyl, bromophenyl, ethoxyphenyl, or benzyl group, etc.

Of these compounds, the Michael acceptors which are apt to be most preferred are (A) those in which T, T', and T" are hydrogen and G is a 'COOR, —C(O)R', or —CN group wherein R and R' are methyl or ethyl and (B) the corresponding compounds in which one or two of the hydrogens represented by T, T', and T' is replaced with a G' electron withdrawing group which may be the same as G or a different group selected from —CN, COOR, and C(O)R'. The especially preferred Michael acceptors are the methyl and ethyl acrylates, acrylonitrile, dicyanoethylene, and tricyanoethylene.

When a single Michael acceptor is employed in the reaction, each T, T', T", and G in the product is the same as each other T, T', T", and G. However, when a mixture of two or more acceptors is used and the different acceptors have different T, T', T", G, and/or G' groups in their molecules, those differences will be reflected in the product. For example, when methyl acrylate and methyl methacrylate are simultaneously or consecutively reacted with a Michael donor, each T and T' in the product molecules will represent hydrogen and each G will represent a —COOCH$_3$ group; but some of the T" groups will represent hydrogen, while the others will be methyl groups. Similarly, when methyl acrylate and acrylonitrile are simultaneously or consecutively reacted with a donor, each T, T', and T" in the product molecules will represent hydrogen; but some of the G groups will be —COOCH$_3$ while others will be —CN.

The reaction between the Michael donor and Michael acceptor is conducted in the presence of a basic compound and a phase transfer catalyst at a suitable temperature, usually a temperature of about 0°–150° C., preferably about 20°–80° C., and most preferably about 40°–60° C.

The basic compound, which serves to initiate the reaction, may be any other suitable base; but it is preferably an alkali or alkaline earth metal hydroxide, alkoxide, amide, or carbonate, more preferably a sodium or potassium hydroxide, alkoxide, amide, or carbonate, and most preferably potassium carbonate. Although it may be used in any amount sufficient to initiate the reaction, its concentration is usually about 1–50%, preferably 3–30%, and most preferably 5–10%, based on the weight of the Michael donor.

The phase transfer catalyst employed in the process may be any such catalyst having sufficient catalytic activity to permit the addition of the desired number of Michael acceptor molecules to the Michael donor at a desired rate. Such catalysts include common phase transfer catalysts such as aluminum oxide, potassium fluoride, and mixtures thereof. However, the preferred catalysts are ordinarily alkylammonium salts such as tetraalkylammonium chlorides, bromides, fluorides, iodides, sulfates, hydrogen sulfates, carbonates, and phosphates in which the alkyl groups contain 1–20 carbons—salts which are frequently used as phase transfer catalysts. The phase transfer catalyst is used in a catalytic amount, typically an amount such as to provide about 0.1–1 mol of catalyst per mol of Michael donor.

Although the Michael reaction of the invention is usually conducted in the absence of a solvent, it may sometimes be desirable to increase the efficiency of the phase transfer reaction by utilizing a solvent. The solvent, when used, should be a non-nucleophilic substance, e.g., a hydrocarbon, which will maintain the reactants in solution during the reaction but permit easy separation of the products from the reaction mixture. Such solvents include, e.g., toluene, xylene, other alkylbenzenes, hexane, and other saturated hydrocarbons.

The reaction is effected by combining the reactants, initiator, and catalyst, optionally in the presence of a solvent, and maintaining contact between the reactants at the selected reaction temperature until the desired degree of reaction has been effected. It is sometimes preferred to make the Michael acceptor the last of the ingredients to be charged to the reaction vessel in order to achieve better control of the reaction temperature and hence improved direction of the reaction to the formation of a desired product.

In the Michael reaction of the invention, the type of product formed is determined largely by the acceptor/donor ratio in the reaction mixture—higher ratios leading to the formation of products containing more acceptor moieties per molecule and thus having higher molecular weights. Since the reaction normally leads to the formation of a mixture of products containing different numbers of acceptor moieties per molecule, it permits the production of some molecules containing more acceptor moieties than the number that would theoretically be provided by the amount of acceptor employed in the reaction mixture. However, it is necessary for the reaction mixture to contain at least the stoichiometric requirement of the acceptor, and preferably a stoichiometric excess, in order for the product to contain a substantial amount of a desired product molecule. Thus, e.g., when it is desired to form a product mixture in which a substantial percentage of the product molecules contain three acceptor moieties, the reaction mixture should contain at least the stoichiometrically required three mols of acceptor/mol of donor and preferably contains >3 mols of acceptor/mol of donor; and, when a substantial number of product molecules containing eight acceptor moieties is desired, it is important for the reaction mixture to contain at least eight tools of acceptor/mol of donor.

Since it is usually preferred for the product molecules to contain about 3–30 acceptor moieties/donor moiety, the acceptor/donor tool ratio in the reaction mixture is most commonly about 3–35/1.

Of the novel products of the invention, those which are preferred are the mixtures of compounds corresponding to the formula Z—C(E)(E')$_p$—Q, in which Z is alkyl, cycloalkyl, or —(CTT'—CT''G)$_w$—CTT'—CHT''G, and Q is —(CTT'—CT''G)$_t$—CTT'——CHT''G, as defined above, and the sum of t and w in at least 25% of the molecules is 1–30, most preferably 1–10.

Such compounds are prepared from the aforementioned Z'—CH(E)(E'') donors and CTT'=CT''G acceptors as illustrated in the following equations:

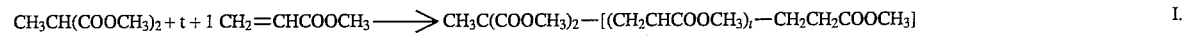

I.

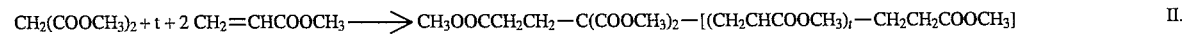

II.

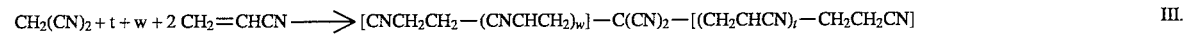

III.

IV.

These reactions are able to proceed until the desired number of acceptor moieties have been combined with the donor, even when the donor contains only one active hydrogen, because the hydrogen donated to an acceptor moiety when the donor is deprotonated becomes an active hydrogen in the acceptor moiety and can be donated to a second moiety where it becomes a donatable hydrogen again. Thus, a reaction such as that summarized in Equation I above would proceed as follows:

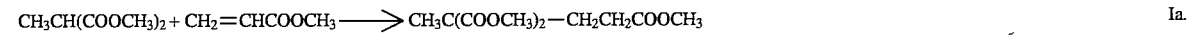

Ia.

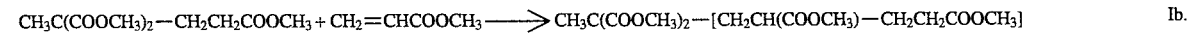

Ib.

Ic.

Id.

and continue in the presence of a sufficient amount of acceptor.

As indicated by Equations II and III above, the incorporation of several acceptor moieties into the product molecules is facilitated by utilizing the more reactive CH$_2$(E)(E'') donors, especially when a CH$_2$=CHG acceptor is employed; and the incorporation of multiple acceptor moieties is also aided by the use of (1) reactants containing the stronger electron withdrawing groups, (2) the higher reaction temperatures, (3) the stronger catalysts, and/or (4) the larger amounts of catalyst. Variations in product structure and properties can be achieved by using mixtures of donor compounds and/or mixtures of acceptor compounds in the reaction.

The products of the Michael reaction may be liquids or solids, depending on the particular reactants and reactant ratios used; and, as already indicated, they are typically mixtures of compounds containing different numbers of acceptor moieties per molecule. Since the individual components of the mixtures can be useful in various applications, they may be isolated from one another if desired. However, the product mixtures themselves —especially those in which at least about 25% of the product molecules contain at least three acceptor moieties—are also useful materials, so such isolations are frequently unnecessary and, in fact, sometimes undesirable. Having a product characterized by a wide molecular weight distribution can be an advantage in providing a balance of properties, as is the case with oils which are to be used in an application wherein some relatively high molecular weight portion is desired to give a required viscosity, but some relatively low molecular weight portion is desired to impart compatibility with a material with which the oil is to be used.

Achieving either a better balance of properties or properties which differ in some other respect from those of the Michael reaction product can also be accomplished by subjecting the product mixture to one or more of the reactions known to be capable of converting functional groups (i.e., E, E', G, and/or G' groups) in the compounds to different groups. Such reactions, like the conversion of lower ester groups to higher ester groups, can be conducted by conventional techniques, such as those indexed and outlined in Harrison and Harrison, *Compendium of Organic Synthetic Methods*, Wiley-Interscience (New York), 1971, the teachings of which are incorporated herein by reference.

In addition to having the aforementioned advantage, the post-treatment of the Michael reaction product to prepare a different product mixture of the invention has the benefit of facilitating the preparation of products which it would be at least more difficult to prepare directly by the Michael reaction. For example, it can be beneficial to use a post-Michael reaction conversion of the functional groups when the desired end product is to contain functional groups which, if present in the Michael reactants, would make the Michael reaction relatively slow. Thus, it is apt to be preferred, for example, to react dimethyl malonate with methyl acrylate to provide a first product of the invention and then transesterify that product with hexanol to provide a second product in which the functional groups are hexyl ester groups than to prepare a Michael reaction product from the slower-reacting dihexyl malonate and hexyl acrylate.

Since the Michael reaction and the post-Michael reaction treatments of the Michael products can be tailored to form products which are liquids or solids having widely different molecular weights, the different products of the invention are useful in a variety of applications—the lower molecular weight products being generally most suitable as plasticizers and solvents, the oils usually serving best as lubricants, and the higher molecular weight solids ordinarily being most suited as plastics.

The Z—C(E)(E')$_p$—Q$_s$ oils, especially the ester oils, constitute a preferred embodiment of the invention. These oils, in addition to having general utility as lubricants, have particular value as refrigeration lubricants, since (1) they can be adapted to have viscosities suitable for refrigeration lubricants (usually 1–600, preferably 5–300, and most preferably 10–200 mm$^2$·s$^{-1}$ at 40° C.), and (2) their high polarity, together with extensive branching and molecular weight tailoring, can make them completely miscible with common refrigerants, e.g., ammonia; alcohols such as methanol and ethanol; glycols such as ethylene and propylene glycols; hydrocarbons such as methane, ethane, propane (R-290), butane, ethylene, and propylene; and halocarbons and/or halohydrocarbons such as chlorotrifluoromethane, dichlorodifluoromethane, dichlorofluoromethane, chlorodifluoromethane(R-22), 1,2,2-trifluoro-1,1,2-trichloroethane, 1,1-dichloro-2,2,2-trifluoroethane (R-123), 1,1-dichloro-1-fluoroethane, 1-chloro-2,2,2-trifluoroethane, 1-chloro-1,2,2,2-tetrafluoroethane (R-124), 1-chloro-1,1,2,2-tetrafluoroethane, dichloromethane, difluoromethane (R-32), 1,1,2,2,2-pentafluoroethane (R-125), 1,1,2,2-tetrafluoroethane (R-134), 1,1,1,2-tetrafluoroethane (R-134a), 1,1,1-trifluoroethane (R-143a), 1,1-difluoroethane (R-152a), and mixtures thereof.

Among the refrigerant blends with which these oils can be advantageously used as lubricants are the binary mixtures of R-32 with R-125, R-152a, or R-134a; R-125/R-143a, R-290/R-134a, and R-22/R-152a binary blends; and ternary blends such as R-22/R-290/R-125, R-22/R-152a/R-124, R-32/R-125/R-134a, and R-125/R-143a/R-134a.

The ability of the present invention to provide lubricants compatible with R-134a is perhaps its most valuable asset, since R-134a has been reported to have an ozone depletion potential of zero, therefore would be environmentally superior to the chlorofluorocarbon refrigerants most commonly used in refrigeration applications, but has the disadvantage of not being compatible with the lubricants normally used in those applications. However, as already mentioned, the ester oils have general utility as lubricants; and they have uses in other applications too. For example, (1) having relatively low volatilities at given viscosities, they can be utilized as hydraulic fluids in metal worldrig, electrical generation, and mining industries, optionally in conjunction with soluble polymers, such as styrene-diene polymers, (2) having a relatively high smoke point for a given viscosity, they can be used in spin finish formulations in the textile industry and in other such applications where it is undesirable to release smoke into the working environment, and (3) those having the best thermal stabilities can also be employed in applications such as turbine oils, rolling oils, and compressor oils.

The ester oils are preferably prepared by (1) reacting a Z'—CH(COOR)$_2$ donor in which Z' is most preferably hydrogen with a CTT'=CT"COOR acceptor to form a Z—C(COOR)$_2$—(CTT'—CT" COOR)$_w$—CTT'—CHT"COOR product which is characterized by (a) being composed primarily of molecules wherein Z is most preferably —(CTT'—CT"COOR)$_t$—CTT'—CHT"COOR, at least some of the Rs (which may be the same or different) are lower alkyls of 1–8 carbons, each of t and w is zero or a positive integer, and the sum of t and w is 0–28 and (b) having at least three acceptor moieties in at least about 25%, preferably at least about 40% of those molecules and (2) when desired (especially when all of the Rs are methyl) transesterifying the resultant intermediate product by reacting it with one or more alcohols containing more carbons per molecule than the lower alkyl groups of the intermediate.

When transesterification is desired, it is accomplished by contacting the intermediate with one or more alcohols containing more carbons per molecule than the alkyl groups to be replaced and maintaining contact between the reactants at a suitable temperature until the desired transesterification has been effected. Alcohols most apt to be desirable for use in the reaction are substituted and unsubstituted alkanols, cycloalkanols, and aralkanols containing up to about 10 carbons (e.g., ethanol, chloroethanol, propanol, butanol, hexanol, bromohexanol, heptanol, octanol, decanol, fluorodecanol, cyclohexanol, cyclooctanol, benzyl alcohol, p-methylbenzyl alcohol, phenethyl alcohol, and phenylpropanol), as well as the aliphatic, cycloaliphatic, and araliphatic alcohols containing up to 10 carbons and also containing hetero atoms, such as oxygen, phosphorus, or sulfur (e.g., ethylthioethanol, ethoxyethanol, and the like).

The amount of alcohol employed in the transesterification reaction varies with the degree of transesterification desired, the quantity generally being the stoichiometric amount or an amount slightly in excess of the stoichiometric requirement. For example, when the intermediate contains an average of four ester groups per molecule, and it is wished to replace substantially all of those ester groups with the alcohol or alcohols used in the transesterification reaction, the amount of alcohol added to the intermediate should be at least four mols/mol of intermediate. Only about half as much alcohol would be added, on the other hand, when the objective is to replace approximately half of the ester groups of the intermediate.

Use of a transesterification reaction after completion of the Michael reaction permits a wide variety of products to be prepared from any particular product of the Michael reaction—final products having only the short ester chains which favor solubility in a refrigerant such as R-134a, final products having only the longer ester chains which increase viscosity, and final products having a controlled mix of short and longer ester chains to provide desired intermediate degrees of solubility and viscosity.

The transesterification is suitably conducted at an elevated temperature which provides for reflux and removal of a lower alcohol by-product from the reaction mixture without permitting undue loss of the higher alcohol reactant(s) from the reaction vessel, e.g., a temperature of about 50°–180° C. Although the reaction does not require catalysis, it is accelerated by the use of a base, which may be the base already present when the Michael reaction product is transesterified without first being recovered from its synthesis reaction mixture. It is sometimes desirable to add a catalytic amount of a base to accelerate the reaction, especially when the Michael product has been recovered before being subjected to transesterification. However, when such an addition is made, the amount of catalyst added is preferably kept low enough to prevent interference with the reaction or with subsequent separation of the products from the reaction mixture. Such an amount is typically about 0.05–1.0 g/kg of the Michael reaction product to be transesterified.

In another preferred embodiment of the invention, reaction products obtained from Michael donors and acceptors in which less than all of the electron withdrawing groups are ester groups (e.g., products obtained from methyl acetoacetate and methyl acrylate and products obtained from dimethyl malonate and methacrylonitrile) are subjected to a transesterification reaction to replace some or all of the ester groups with higher ester groups. Desirable ester products can also be obtained by subjecting a Michael reaction product containing nitrile groups to simultaneous hydrolysis and esterification with one or more alcohols in order to replace some or all of the nitrile groups with ester groups.

The products resulting from the Michael reaction or from conversion of the Michael reaction products to derivatives are typically washed with water to remove any unreacted materials and catalyst prior to being used in their intended application; and, if desired, they may then be further purified by subjecting them to fractional distillation. They may then be utilized alone or together with other materials serving similar functions and/or with additives serving other functions in their intended application, e.g., as plasticizers, solvents, lubricants, molding materials, or any of the other uses mentioned above.

Additives particularly apt to be used together with the products of the invention are (1) the antioxidants frequently used in organic compositions, (2) epoxy and other dehydrating agents sometimes used in refrigeration compositions, and (3) the oxidation resistance and thermal stability improvers, corrosion inhibitors, metal deactivators, lubricity additives, viscosity index improvers, pour and/or floc point depressants, detergents, dispersants, antifoaming agents, anti-wear agents, and extreme pressure resistance additives conventionally used in lubricant compositions. Also, when used as refrigeration lubricants, they are used in conjunction with refrigerants (such as those mentioned above), although they can be mixed with the refrigerants in situ rather than being combined with them prior to use.

The following examples are given to illustrate the invention and are not intended as a limitation thereof.

EXAMPLE 1

Charge a suitable reaction vessel with 792 g (6 mols) of dimethyl malonate, 52.8 g (0.4 mol) of potassium carbonate, 12 g (0.035 mol) of tetrabutylammonium hydrogen sulfate, and 1290 g (15 mols) of methyl acrylate. After stirring the reaction mixture at room temperature for ~18 hours, slowly heat it to ~50° C. to effect a rapid rise of the temperature of the reaction mixture to reflux. Maintain the reaction mixture at reflux for ~15 minutes and then cool to room temperature over a period of ~1 hour. A heavy solid mass forms in the bottom of the reaction vessel during cooling. Dilute this mass with methylene chloride, wash with five 1.5-L portions of water, and subject the product to gas chromatographic (GC) analysis. The analysis shows the product to consist, in area percentages, of 4.3% trimethyl ester of 1,1,3-propanetricarboxylic acid, 70% tetramethyl ester of 1,3,3,5-pentanetetracarboxylic acid, 18% pentamethyl ester of 1,3,3,5,7-heptanepentacarboxylic acid, and 7.7% polyesters, i.e., products having more than five ester groups per molecule.

EXAMPLE 2

Conduct two additional Michael reactions between dimethyl malonate and methyl acrylate using tetrabutylammonium hydrogen sulfate as the phase transfer catalyst as in Example 1 but employing sodium methoxide as the base, 80° C. as the reaction temperature, and methyl acrylate/dimethyl malonate tool ratios of 8/1 (reaction mixture 2-A) and 10/1 (reaction mixture 2-B) respectively. Monitor the reactions by GC and discontinue them when the following analyses are obtained:

| | |
|---|---|
| Reaction mixture 2-A: | 32% tetramethyl ester of 1,3,3,5-pentanetetracarboxylic acid, 24% pentamethyl ester of 1,3,3,5,7-heptanepentacarboxylic acid, 11% hexamethyl ester of 1,3,5,5,7,9-nonanehexacarboxylic acid, 8% heptamethyl ester of 1,3,5,5,7,9,11-undecaneheptacarboxylic acid, 2% octamethyl ester of 1,3,5,7,7,9,11,13-tridecaneoctacarboxylic acid, and smaller amounts of higher esters |
| Reaction mixture 2-B: | 20% tetramethyl ester, 22% pentamethyl ester, 19% hexamethyl ester, 14% heptamethyl ester, 9% octamethyl ester, and smaller amounts of higher esters |

Then work up the product mixtures by diluting them with solvent, washing to neutrality with water, and removing solvent, water, and lower boiling products by distillation to form viscous oils which, in each case, are completely miscible with R-134a over a temperature range of −40° C. to 70° C.

EXAMPLE 3

Charge a suitable reaction vessel with 660 g (5 mols) of dimethyl malonate, 35 g (0.25 mol) of potassium carbonate, and 1.75 g (0.005 mol) of tetrabutylammonium hydrogen sulfate. Heat the stirred mixture to 120° C., and add 2048 g (16 mols) of n-butyl acrylate over a period of six hours while monitoring the reaction by GC, which shows the dibutyl dimethyl ester of 1,3,3,5-pentanetetracarboxylic acid to be the major product at the end of this period. Then heat the reaction mixture at 150° C. for three hours to form a product mixture containing the tributyl dimethyl ester of 1,3,3,5,7-heptanepentacarboxylic acid. Cool the resulting reaction mixture to room temperature, add water and toluene, wash repeatedly with water until neutral, remove the water and toluene by azeotropic distillation, and then remove light products at 180°–185° C. and 0.1–0.15 mmHg to provide a heavy oil having a viscosity of 96 $mm^{2 \cdot at}$ 40° C., a viscosity of 11.6 $mm^{2} \cdot s^{-1}$ at 100° C., a viscosity index of 109, and excellent miscibility with R-134a over a temperature range of -60° C to 80° C.

EXAMPLE 4

Using a dimethyl malonate/methyl acrylate Michael reaction and workup procedure similar to that of the preceding examples, prepare a 20.8 g sample of a mixture of 66% tetramethyl ester of 1,3,3,5-pentanetetracarboxylic acid, 26% pentamethyl ester of 1,3,3,5,7-heptanepentacarboxylic acid, and 6% hexamethyl and heptamethyl esters. Treat the mixture with 0.1 mol of butanol and 0.1 mol of hexanol at 120° C. in the presence of a catalytic amount of 10% sodium methoxide, remove the volatiles by distillation, and work up to provide an oil which has a viscosity of 159 $mm^{2} \cdot s^{-1}$ at 40° C, a viscosity of 14.6 $mm^{2} \cdot s^{-1}$ at 100° C., a viscosity index of 88, and total miscibility with R-134a.

EXAMPLE 5

Charge a reaction vessel with 15.8 Kg (120 mols) of dimethyl malonate, 158 g (1.2 mols) of potassium carbonate, and 37 g (0.1 mol) of tetrabutylammonium hydrogen sulfate under nitrogen. Heat the reactor to ~70° C., add 25.8 Kg (300 mols) of methyl acrylate over six hours, and then heat the reaction mixture at 70°–80° C. for at least 10 hours to form a product mixture containing a major amount of tetramethyl ester of 1,3,3,5-pentanetetracarboxylic acid, smaller amounts of pentamethyl and higher esters, and a minor amount of trimethyl ester of 1,1,3-propanetricarboxylic acid.

Charge 22 Kg (296 mols) of n-butanol and 30.3 Kg (296 mols) of n-hexanol to the reactor and heat at 110°–120° C. while collecting the volatiles overhead. After removing the stoichiometric amount of methanol, cool the reaction mixture to room temperature, dilute with toluene, wash to neutrality with water, dry by the azeotropic removal of water, and heat treat the crude under reduced pressure.

Distillation under reduced pressure (1 mmHg) and 200°–250° C. provides an oil which has a viscosity of 17 mm$^2 \cdot$s$^-$ at 40° C., a viscosity of 3.6 mm$^2 \cdot$s$^{-1}$ at 100° C., number (TAN) of 0.025 mgKOH/g, a water content of 64 ppm, and total miscibility with R-134a over a temperature range of —60° C. to 80° C. The bottoms product is an oil having a viscosity of 24.8 mm2.s$^{-1}$ at 40° C., a viscosity of 4.7 mm$^2 \cdot$s$^{-1}$ at 100° C., a number of 0.034 mgKOH/g, a water content of 73 ppm, and total miscibility with R-134a over a temperature range of —60° C. to 80° C.

EXAMPLE 6

Charge a reaction vessel with 3.3 g (0.05 mol) of malononitrile, 0.7 g (0.005 mol) of potassium carbonate, and 0.17 g (0.5 mmol) of tetrabutylammonium hydrogen sulfate under nitrogen. Slowly add 11.2 g (0.2 mol) of acrylonitrile at 50° C. with stirring and maintain the temperature at 50°–70° C. for 3 hours. Then cool the reaction mixture to room temperature, dissolve in ethyl acetate, wash with water until neutral, dry over magnesium sulfate, filter, and concentrate to provide a solid mass which spectroscopic analysis indicates to contain more than two acrylonitrile moieties per molecule.

EXAMPLE 7

Charge a reaction vessel with 3.3 g (0.05 mol) of malononitrile, 0.7 g (0.005 mol) of potassium carbonate, and 0.17 g (0.5 mmol) of tetrabutylammonium hydrogen sulfate. Heat the mixture to 50° C. under nitrogen and slowly add 10.8 g (0.125 mol) of methyl acrylate at a rate such as to maintain the temperature under 80° C. Keep the reaction mixture at 70°–80° C. for two hours, cool to room temperature, dilute with dichloromethane, wash with water until neutral, dry over magnesium sulfate, filter, and concentrate to provide a solid mass which spectroscopic analysis shows to contain dimethyl ester of 3,3-dicyano-1,5-pentanedicarboxylic acid, trimethyl ester of 5,5-dicyano-1,3,7-heptanetricarboxylic acid, and smaller amounts of higher molecular weight components.

What is claimed is:

1. A mixture of compounds corresponding to the formula Z—C(E)(E')$_p$—Q$_s$, wherein Z is alkyl, cycloalkyl, or —(CTT'—CT"G)$_w$—CTT'CHT"G; Q is —(CTT'—CT"G)$_t$—CTT'—CHT"G; T, T', and T" are independently selected from hydrogen, G', and hydrocarbyl or predominantly hydrocarbyl organic groups containing up to 10 carbons, with the proviso that at least one of T, T', and T" must be hydrogen; E, E', G, and G' are independently selected from —COOR, —C(O)R', and —CN electron withdrawing groups in which R and R' represent alkyl or cycloalkyl groups of up to 10 carbons; p is zero or one; s is respectively two or one; and each of t and w represents zero or a positive integer; at least two compounds in the mixture containing a different number of G groups and at least 25% of the molecules of the compounds containing at least three G groups.

2. The mixture of claim 1 wherein p and s are one, Z is —(CTT'—CT"G)$_w$—CTT'—CHT"G, and the sum of t and w in at least 25% of the molecules is 1–30.

3. The mixture of claim 2 wherein the sum of t and w in at least 25% of the molecules is 1–10.

4. The mixture of claim 2 wherein at least one of the E and G groups is —COOR.

5. The mixture of claim 4 wherein the sum of t and w in at least 25% of the molecules is 1–10.

6. The mixture of claim 4 wherein Z is —(CH$_2$CT"COOR)$_w$—CH$_2$CHT"COOR; Q is —(CH$_2$CT"COOR)$_t$—CH$_2$CHT"COOR; T" is independently selected from hydrogen and alkyls of 1–10 carbons; E and E' are —COOR groups; and the —COOR groups of Z, Q, E, and E' are independently selected from —COOR groups in which R is an alkyl of 1–10 carbons.

7. The mixture of claim 6 wherein the sum of t and w in at least 25% of the molecules is 1–10.

8. The mixture of claim 7 wherein each T" is hydrogen.

9. The mixture of claim 7 wherein each T" is alkyl.

10. The mixture of claim 7 wherein the molecules contain at least two different T" groups, one of which is hydrogen.

11. The mixture of claim 1 wherein s is two, Z is —(CTT'—CT"G)$_w$—CTT'—CHT"G, and the sum of t and w in at least 25% of the molecules is 0–30.

12. The mixture of claim 11 wherein the sum of t and w in at least 25% of the molecules is 1–10.

13. The mixture of claim 11 wherein at least one of E and G is —COOR.

14. The mixture of claim 13 wherein the sum of t and w in at least 25% of the molecules is 1–10.

* * * * *